(12) United States Patent
Faryniarz et al.

(10) Patent No.: US 7,445,729 B2
(45) Date of Patent: *Nov. 4, 2008

(54) STABLE ORGANIC PEROXIDE COMPOSITIONS

(75) Inventors: Joseph R. Faryniarz, Middlebury, CT (US); Jose E. Ramirez, Trumbull, CT (US)

(73) Assignee: JR Chem, LLC, Key West, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 11/986,442

(22) Filed: Nov. 21, 2007

(65) Prior Publication Data

US 2008/0067474 A1    Mar. 20, 2008

Related U.S. Application Data

(63) Continuation of application No. 11/476,527, filed on Jun. 28, 2006, now abandoned.

(60) Provisional application No. 60/695,223, filed on Jun. 29, 2005.

(51) Int. Cl.
  *C01B 15/10*   (2006.01)
  *C09K 15/08*   (2006.01)
  *A61K 8/38*    (2006.01)

(52) U.S. Cl. .................. 252/186.26; 252/186.42; 252/404; 252/407; 424/401; 424/404; 424/78.01; 514/714; 514/718; 514/731; 514/846; 514/859; 514/937; 514/938

(58) Field of Classification Search ............ 252/186.26
See application file for complete search history.

(56) References Cited

U.S. PATENT DOCUMENTS

| | | | |
|---|---|---|---|
| 3,538,011 A | 11/1970 | Van der Klaauw | |
| 3,887,652 A | 6/1975 | Carrock et al. | |
| 4,056,611 A | 11/1977 | Young | |
| 4,318,907 A | 3/1982 | Kligman et al. | |
| 4,350,681 A | 9/1982 | Fulton, Jr. | |
| 4,387,107 A * | 6/1983 | Klein et al. | 514/714 |
| 4,416,873 A | 11/1983 | Puchalski et al. | |
| 4,440,885 A | 4/1984 | Tamosauskas | |
| 4,497,794 A | 2/1985 | Klein et al. | |
| 4,520,133 A | 5/1985 | Dines et al. | |
| 4,593,046 A | 6/1986 | Gruber | |
| 4,608,392 A | 8/1986 | Jacquet et al. | |
| 4,609,674 A | 9/1986 | Gupte | |
| 4,640,932 A | 2/1987 | Fong et al. | |
| 4,664,847 A | 5/1987 | Williams | |
| 4,692,329 A | 9/1987 | Klein et al. | |
| 4,725,429 A | 2/1988 | Scott et al. | |
| 4,767,750 A | 8/1988 | Jacquet et al. | |
| 4,803,228 A | 2/1989 | Jacquet et al. | |
| 4,844,886 A | 7/1989 | Hartmann et al. | |
| 4,857,302 A | 8/1989 | Decker, Jr. et al. | |
| 4,906,617 A | 3/1990 | Jacquet et al. | |
| 4,923,900 A | 5/1990 | De Villez | |
| 4,925,666 A | 5/1990 | Decker, Jr. et al. | |
| 4,959,205 A | 9/1990 | Brunner et al. | |
| 4,960,772 A | 10/1990 | Sebag et al. | |
| 5,019,567 A | 5/1991 | Philippe et al. | |
| 5,086,075 A | 2/1992 | De Villez | |
| 5,409,917 A | 4/1995 | Robinson et al. | |
| 5,466,446 A | 11/1995 | Stiefel et al. | |
| 5,514,670 A | 5/1996 | Friedman et al. | |
| 5,545,407 A | 8/1996 | Hall et al. | |
| 5,607,980 A | 3/1997 | McAtee et al. | |
| 5,612,324 A | 3/1997 | Guang Lin et al. | |
| 5,621,006 A | 4/1997 | Yu et al. | |
| 5,632,996 A | 5/1997 | Ramirez et al. | |
| 5,637,354 A | 6/1997 | Segalla | |
| 5,690,946 A | 11/1997 | Koulbanis et al. | |
| 5,733,886 A | 3/1998 | Baroody et al. | |
| 5,767,098 A | 6/1998 | Klein et al. | |
| 5,789,445 A | 8/1998 | Schweiger | |
| 5,879,716 A | 3/1999 | Katz et al. | |
| 5,894,019 A | 4/1999 | Hesse et al. | |
| 5,910,312 A | 6/1999 | Fried | |
| 5,912,255 A | 6/1999 | Bussell | |
| 5,916,574 A | 6/1999 | Fried et al. | |
| 5,948,416 A | 9/1999 | Wagner et al. | |
| 5,993,833 A | 11/1999 | De Lacharriere et al. | |
| 5,997,885 A | 12/1999 | Koulbanis et al. | |
| 6,117,843 A | 9/2000 | Baroody et al. | |
| 6,277,892 B1 | 8/2001 | Deckner et al. | |
| 6,369,247 B1 | 4/2002 | Miller et al. | |
| 6,433,024 B1 | 8/2002 | Popp et al. | |
| 6,448,233 B1 | 9/2002 | Lefevre et al. | |

(Continued)

FOREIGN PATENT DOCUMENTS

WO    WO 03039510 A1    5/2003

OTHER PUBLICATIONS

1995 U.S. Pharmacopeia/National Formulary USP 23/NF 18, pp. 179-180.

(Continued)

*Primary Examiner*—Joseph D Anthony
(74) *Attorney, Agent, or Firm*—Carter, DeLuca, Farrell & Schmidt, LLP

(57) ABSTRACT

Organic peroxide compositions are stabilized against decomposition by the use of antioxidants, resulting in increased shelf life of products made using the compositions.

13 Claims, No Drawings

U.S. PATENT DOCUMENTS

| | | |
|---|---|---|
| 6,482,431 B2 | 11/2002 | Smith |
| 6,596,287 B2 | 7/2003 | Deckers et al. |
| 6,713,075 B2 | 3/2004 | Bekele |
| 6,737,070 B1 | 5/2004 | Burkhart |
| 6,740,330 B1 | 5/2004 | Bernstein |
| 6,762,158 B2 | 7/2004 | Lukenbach et al. |
| 6,878,378 B1 | 4/2005 | Yamaki et al. |
| 6,896,890 B2 | 5/2005 | Singh et al. |
| 7,153,888 B2 | 12/2006 | Schwarz et al. |
| 2002/0048558 A1 | 4/2002 | Niemiec et al. |
| 2003/0064084 A1 | 4/2003 | Bhagwat et al. |
| 2004/0101566 A1 | 5/2004 | Cooper et al. |
| 2004/0170659 A1 | 9/2004 | Bhagwat et al. |
| 2004/0211938 A1 | 10/2004 | Bock et al. |
| 2004/0223900 A1 | 11/2004 | Khabashesku et al. |
| 2006/0135822 A1 | 6/2006 | Schwarz et al. |
| 2007/0003504 A1 | 1/2007 | Ramirez et al. |

OTHER PUBLICATIONS

T.W. Graham Solomons, Fundamentals of Organic Chemistry, 1997, John Wiley & Sons, Inc., Fifth Edition, pp. 620-621, 640-641, 668, 760.

* cited by examiner

STABLE ORGANIC PEROXIDE COMPOSITIONS

CROSS REFERENCE TO RELATED APPLICATION

This application is a continuation and claims priority benefit of U.S. application Ser. No. 11/476,527 filed Jun. 28, 2006 now abandoned which claims priority to U.S. Provisional Application No. 60/695,223 filed Jun. 29, 2005. The entire disclosures of these prior applications are incorporated herein by reference.

BACKGROUND

1. Technical Field

This disclosure relates to the preparation of compositions containing stable organic peroxide in solution. The compositions are useful for topical application to human skin and/or allow stable organic peroxides to be utilized in new product forms. Products (e.g., industrial, pharmaceutical or consumer based products) formulated using these compositions exhibit extended shelf life. Such compositions also have unique processing capabilities.

2. Background of Related Art

Organic peroxides are used in many products. For example, benzoyl peroxide is used in pharmaceutical and consumer products as an active ingredient for therapeutic treatments. Organic peroxides are unstable. This instability is a desired trait when these materials are used for free radical initiation. When organic peroxides are used for purposes other than free radical initiation, however, it is desirable to have the material be as stable as possible. Instability is problematic and leads to short shelf lives, required expiration dating, higher product costs, special storage considerations, product returns as well as reduced efficacy due to loss of active.

Accordingly, what are needed are compositions of organic peroxides with improved stability for use in products where increased shelf life would be an advantage.

SUMMARY

Organic peroxide compositions including one or more antioxidants are described herein. These compositions exhibit excellent stability. Such compositions can be formulated into products with increased shelf life. The excellent stability also leads to product forms that were previously not obtainable, such as, for example, solutions of benzoyl peroxide (a material which is inherently unstable when stored at elevated temperatures). The present compositions may further include a solvent constituent in which the organic peroxide is soluble. Moreover, the compositions have been found to be useful in forming organic peroxide containing emulsions.

In embodiments, suitable stable corrective compositions in accordance with the present disclosure provide a solvent vehicle formulation for the treatment of acne in which the major active ingredient is benzoyl peroxide. The benzoyl peroxide is provided in clear product forms such as serums, toners, pump or aerosol sprays, clear gels, sticks, creams, lotions and mousses. The clear product forms can be incorporated into other pharmaceutical or cosmetic product forms such as emulsions.

In some embodiments, compositions include a stable mixture of organic peroxide and antioxidant. The weight ratio of organic peroxide to antioxidant may be about 2.5:1 to about 10:1. The composition may include a solvent in which the organic peroxide is soluble. Furthermore, the organic peroxide, such as benzoyl peroxide, may be a liquid in which antioxidant is soluble. In other embodiments, the organic peroxide may be a solid in which antioxidant can be dispersed.

These and other aspects of this disclosure will be evident upon reference to the following detailed description.

DETAILED DESCRIPTION OF PREFERRED EMBODIMENTS

Compositions in accordance with this disclosure include at least one antioxidant in combination with one or more organic peroxides. The antioxidant may be any of the type materials that are soluble in the solvent carrier for the desired organic peroxide, and/or soluble or dispersible in the organic peroxide itself. Suitable non-limiting examples of antioxidants for oil soluble systems include, but are not limited to, butylated hydroxyl toluene (BHT), butylated hydroxyanisole (BHA), vitamin E acetate, ascorbyl palmitate, tetrahydrocurcuminoids, t-butyl hydroquinone, meta and para cresols, phenolics and the like, and combinations of these antioxidants. It should, of course, be understood that combinations of antioxidants can be used in making the present compositions and/or formulations. The amount of antioxidant employed in the composition will depend on a number of factors including, but not limited to the nature of the organic peroxide, the concentration of the organic peroxide, the nature of any solvents present and the nature of the ultimate product to be formulated using the composition. Typically however, the antioxidant is present in an amount of about 0.1 to 30 percent by weight of the total composition. In particularly useful embodiments, the antioxidant is present in an amount of about 1.0 percent to 10 percent by weight of the total composition.

Organic peroxides have long been used in industry to initiate free radical polymerization of unsaturated monomers. The free radical that is formed from the decomposition of the peroxide attaches itself to an unsaturated carbon of the monomer with its electron rich double bond. The free electron then causes an electron shift to the carbon adjacent to where the double bond existed. This unpaired electron forms an unstable free radical and requires another electron to be paired with it. The new free radical will now seek out another double bonded carbon to which it can attach. This process repeats itself until the monomer is depleted or the polymer chain encounters a species of molecule that stabilizes the free radicals.

Organic peroxide refers generally to any organic molecule containing the peroxide functional group ROOR'. Suitable non-limiting examples of organic peroxides for use in accordance with the present disclosure include any in the following classes: diacyl, dialkyl, hydroperoxides, ketone peroxides, peroxyesters, peroxyketals, peroxydicarbonates, and combinations thereof. Additional non-limiting examples of organic peroxides include acetone peroxide, benzoyl peroxide, cumene hydroperoxide, methyl ethyl ketone peroxide, pinane peroxide, diethyl ether peroxide. In embodiments, the organic peroxide is benzoyl peroxide. The amount of organic peroxide employed in the composition will depend on a number of factors including, but not limited to the nature of the organic peroxide, the concentration of the organic peroxide, the nature of any solvents present and the nature of the ultimate product to be formulated using the composition. Typically however, the organic peroxide will be present in an amount of about 1 to 70 percent by weight of the total composition. In particularly useful embodiments, the organic peroxide will be present in an amount of about 2 to 35 percent by weight of the total composition.

In embodiments, compositions in accordance with the present disclosure include benzoyl peroxide with one or more antioxidants. Benzoyl peroxide is normally commercially available as either pure (98% active) crystals or in a wet crystalline state containing 70 to 80% active benzoyl peroxide in 20-30% water. Such benzoyl peroxide products are commercially available from The Norac Company Inc., Azusa, Calif. under the BENOX® trade names or from Elf Atochem North America, Inc., Philadelphia, Pa. under the LUCIDOL® trade names. Any of these or other forms of benzoyl peroxide can be mixed with the disclosed solvents to form compositions in accordance with this disclosure.

The amount of benzoyl peroxide mixed with the antioxidant will vary depending on a number of factors, including, for example, the activity of benzoyl peroxide, the ultimate form of the product and the particular disclosed solvent employed. Generally, the benzoyl peroxide will be present in an amount of about 1 to about 70 weight percent of the benzoyl peroxide/antioxidant mixture. In embodiments, the benzoyl peroxide is present in an amount of about 2 to about 35 weight percent of total composition. In embodiments, the benzoyl peroxide is present in an amount of about 2 to about 15 weight percent of the total composition.

The use of benzoyl peroxide in pharmaceutical industry is based on several chemical properties. Benzoyl peroxide is considered a mild antimicrobial compound that will control P. Acnes bacteria. Benzoyl peroxide free radicals can attack the cell walls of the bacteria thus destroying the bacteria. Secondly, the decomposition of the benzoyl peroxide will result in forming benzoic acid, benzene, phenyl benzoate and biphenyls, all such materials can be toxic to cell. Lastly, it has even been proposed that because anaerobic P. Acnes cannot live in the presence of oxygen, oxygen available from the benzoyl peroxide may also kill the bacteria. The exact mechanism for the antimicrobial properties for benzoyl peroxide is however unknown. What is known is that chemical reactions take place on an individual molecular level. Molecules in solution will react much more readily than in solid crystal form.

The individual molecules present in a solution will penetrate the skin much easier than a particulate dispersion. Secondly the benzoyl peroxide in solution form is much more mobile and reactive than is the crystalline form. This increased mobility and reactivity can lead to much more effective products. However this increased mobility and reactivity has the negative of reduced chemical stability in the solution.

Thus, while the use of an antioxidant in accordance with the present disclosure can be used to improve the stability of organic peroxides in any type of composition, such as for example, emulsions or suspensions, in particularly useful embodiments, the antioxidants are used to stabilize organic peroxides in solutions of the organic peroxide.

The decomposition of the organic peroxide (although believed to be desired in order to achieve effectiveness) must be controlled in order to allow use of solutions while providing sufficient storage life. Decomposition of organic peroxides can occur via a variety of mechanisms, such as the following three mechanisms 1. The thermolysis decomposition of diacyl peroxide (benzoyl peroxide is given below):

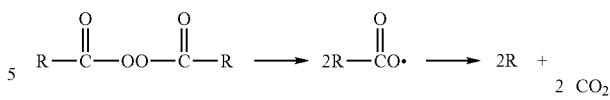

2. Induced decomposition is represented by the following equation where a free radical attacks a peroxide to generate and ester and a different free radical, but no carbon dioxide.

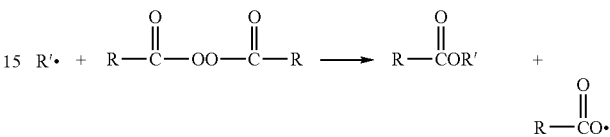

3. Heterolytic decomposition which can occur when strong acids or polar solvents are present.

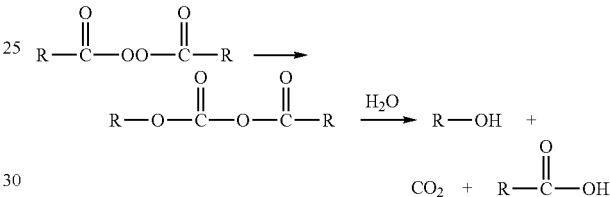

Organic peroxides will have different stability depending on a variety of factors including, but not limited to solvent type, solvent polarity, impurities, peroxide concentration and the occurrence of radical-induced decomposition. Peroxides decompose in more polar or polarizable solvents. Solvents such as benzoates have greater solution stability, which may be attributed to the delocalized electrons of the benzene ring.

Without being bound by any particular theory, using reducing agent antioxidants in solutions with oxidizer organic peroxides can be used to decrease the effects of thermal decomposition. Antioxidants are normally used as sacrificial materials that are more easily oxidized over the material that is to be protected. For some unknown reason, the quenching of the free radicals formed, prevents the further decomposition of the organic peroxide. As seen from the equations for decomposition mechanisms listed above, the generation of carbon dioxide gas is possible by thermolysis or heterolytic decomposition. The heterolytic decomposition reaction does not involve generation of a free radical so it is not evident that use of an antioxidant will affect this reaction outcome. In thermolysis, the free radical is a direct consequence of the peroxide splitting at the oxygen bonds. The antioxidant might prevent the intermediate free radical from further splitting and giving off $CO_2$, but does not give an indication that the organic peroxide would be kept from splitting in the first place.

The reduced decomposition of the organic peroxide provided by the present compositions improves the shelf life of products formulated using the compositions, a result which would not normally be obtained. It has been found that the degree to which carbon dioxide gas is generated provides direct evidence of the degree of stability of the organic peroxide. Stability was also determined experimentally by analytical analysis. Accordingly, methods are available to compare the stability of a first composition containing organic peroxide with the stability of a second composition containing organic peroxide and an antioxidant. By monitoring the amount of carbon dioxide by the first and second compositions, one can easily compare stability. The generation of less carbon dioxide has been found to indicate greater stability of the organic peroxide composition. In the case where organic peroxide contains an antioxidant, relatively smaller amounts of carbon dioxide will be generated indicating that the composition is stable. In cases where an organic peroxide is combined with a solvent, and no antioxidant is present, higher volumes of carbon dioxide will be generated, indicating that the organic peroxide is unstable. Suitable carbon dioxide tests for comparing stability of organic peroxides are further described in the examples below.

In certain embodiments of the present compositions, the ratio of organic peroxide to antioxidant is about 10:1 by weight of the composition, as well as about 2.5:1 by weight of the composition. In embodiments, suitable compositions include a stable mixture of organic peroxide and antioxidant, wherein the weight ratio of organic peroxide to antioxidant is about 2.5:1 to about 10:1. In other embodiments, the composition is a solution having less than 2% antioxidant, and no more than about 10% organic peroxide. However other suitable embodiments such as solutions have an amount of about 5 to 10% antioxidant, and no more than about 20% organic peroxide. In other solution embodiments, the compositions may have a ratio of organic peroxide to antioxidant between about 10:1 by weight of the composition. Still yet, other solution embodiments have a ratio of organic peroxide to antioxidant between about 2.5:1 by weight of the composition. In embodiments, suitable solutions include a stable mixture of organic peroxide and antioxidant, wherein the weight ratio of organic peroxide to antioxidant is about 2.5:1 to about 10:1. In a typical preparation process, the organic peroxide is dissolved into a solvent to the limits of solubility. The additional ingredients and the antioxidants can then be added to the composition to formulate the final desired product.

Solvents useful for preparing solutions in accordance with the present disclosure include any solvent capable solubilizing the organic peroxide. Non-limiting examples of such solvents include short chain alkyl esters, ethers, aldehydes, ketones or alcohols of benzoic acid, benzyl alcohol, salicylic acid, phenol or phathalic acid. As used herein "short chain" refers to a molecule having two to six carbon atoms (C2-C6). Other suitable solvents include aryl esters, ethers, aldehydes, ketones and alcohols of benzoic acid, benzyl alcohol, salicylic acid, phenol and phthalic acid. In certain embodiments, the compositions in accordance with the present disclosure include one or more of the following classes of solvent: alkyl esters of benzoic acid, alkyl esters of benzyl alcohol, alkyl esters of salicylic acid, alkyl esters of phenol, alkyl esters of phthalic acid, alkyl ethers of benzyl alcohol, alkyl esters of phthalic acid, alkyl ethers of benzyl alcohol, alkyl ethers of phenol. Additional non-limiting examples of suitable solvents include benzoyl benzoate, benzoyl alcohol, diethyl phthalate, benzoic acid 2-phenyl ethyl ester, methyl salicylate, ethyl salicylate, propyl salicylate, butyl salicylate, ethyl benzoate, methyl benzoate, propyl benzoate, butyl benzoate, dimethyl phthalate, diethyl phthalate, benzyl ethyl ether, benzyl methyl ether, phenetole, phenyl acetone, phenyl ethyl alcohol, phenoxyethanol, phenyl acetaldehyde, ethyl phenyl acetate, phenyl methyl ketone, phenyl acetate, benzyl acetate, benzyl aceto acetate, benzyl formate, benzaldehyde, benzyl alcohol, ethyl benzyl alcohol, salicylaldehyde, benzyl salicylate, phenyl tolyl ketone, phenyl benzoate, phenyl ether, dibenzyl ether, benzyl benzoate, benzoic acid and 2-phenyl ethyl ester.

The amount of solvent mixed with the organic peroxide will vary depending on a number of factors, including, for example, the ultimate form of the product and the particular solvent employed. Generally, the solvent will be present in an amount of about 1 to about 70 weight percent of the total organic peroxide/solvent mixture. In embodiments, the solvent will be present in an amount of about 10 to about 50 weight percent of the total composition. In embodiments, the solvent will be present in an amount of about 20 to about 40 weight percent of the total composition. In embodiments, solvent is present in amounts effective for dissolving organic peroxide.

In addition to the solvent in which organic peroxide is soluble, the compositions in accordance with the present disclosure may contain one or more secondary solvents. Suitable secondary solvents include, for example, ethanol, acetone, dimethyl isosorbide, and glycol ethers of $C_1$ to $C_6$ alcohols with no greater than 2 moles of ethylene oxide. Suitable glycol ethers include glycol ethers of phenol with no greater than 2 moles of ethylene oxide, glycol ethers of methanol with no greater than 2 moles of ethylene oxide, glycol ethers of ethanol with no greater than 2 moles of ethylene oxide and glycol ethers of propanol with no greater than 2 moles of ethylene oxide. Non-limiting examples of such co-solvents include phenoxy ethanol, ethoxy diglycol and propylene glycol methyl ether.

The amount of secondary solvent mixed with the organic peroxide/solvent mixture will vary depending on a number of factors, including, for example, the ultimate form of the product and the particular solvent and/or secondary solvent employed. Generally, the secondary solvent will be present in an amount of about 1 to about 40 weight percent of the total composition. In embodiments, the secondary solvent will be present in an amount of about 5 to about 30 weight percent of the total composition. In embodiments, the secondary solvent will be present in an amount of about 10 to about 20 weight percent of the total composition.

In embodiments, thickeners and/or rheology modifiers such as fumed silica may be added to the organic peroxide solutions of the present disclosure to increase the viscosity of the compositions and/or gel the compositions. In embodiments, the thickener and/or rheology modifiers may be present in an amount of about 0.1 to about 10 weight percent of the total composition. Any thickener or rheology modifier can be used so long as it does not react with the organic peroxides.

The organic peroxide corrective compositions and/or stable mixtures of organic peroxide and antioxidant in accordance with the present disclosure can be added to product forms. In embodiments, products containing organic peroxide compositions in accordance with the present disclosure can be in the form of solutions, emulsions (including microemulsions), suspensions, creams, fluid cream, oils, lotions, gels, powders, sticks, or other typical solid or liquid compositions used for treatment of undesirable skin conditions. Such compositions may contain, in addition to the organic peroxide and/or organic peroxide compositions in accordance with this disclosure, other ingredients typically used in such products, such as other active cosmetic substances such as retinol, retinol derivatives, allantoin, tocopherol, tocopherol derivatives, niacinamide, phytosterols, isoflavones, panthenol, panthenol derivatives, bisabolol, farnesol, and combinations thereof, other active drug substances such as corticosteroid, metronidazole, sulfacetamide, sulfur, and combinations thereof, antioxidants, antimicrobials, coloring agents, detergents, dyestuffs, emulsifiers, emulsifying wax, emollients, fillers, fragrances, gelling agents, hydration agents, moisturizers, odor absorbers, natural or synthetic oils, penetration agents, powders, preservatives, solvents, surfactants, thickeners, viscosity-controlling agents, water, distilled water, waxes, and optionally including anesthetics, anti-itch actives, botanical extracts, conditioning agents, darkening or lightening agents, glitter, humectant, mica, minerals, polyphenols, phytomedicinals, silicones or derivatives thereof, skin protectants, sunblocks, vitamins, and mixtures or combinations thereof. Such compositions may also contain, in addition to the organic peroxide and/or organic peroxide compositions in accordance with this disclosure, one or more: fatty alcohols, fatty acids, organic bases, inorganic bases, wax esters, steroid alcohols, triglyceride esters, phospholipids, polyhydric alcohol esters, fatty alcohol ethers, hydrophilic lanolin derivatives, hydrophilic beeswax derivatives, cocoa butter waxes, silicon oils, pH balancers, cellulose derivatives, hydrocarbon oils, or mixtures and combinations thereof.

In embodiments, product forms can be formulated to contain humectant in amounts from about 1% to about 15% by weight of the total composition. For example glycerin can be added to the composition in amounts from about 1% to about 15% by weight of the total composition. In particular embodiments, glycerin can be added to the composition in amounts from about 1% to about 5% by weight of the total composition.

In embodiments, product forms can be formulated to contain solvent in an amount of about 1% to about 45% by weight of the total composition. For example petroleum derivatives such as propylene glycol can be added to the composition in an amount of about 1% to about 45% by weight of the total composition. In particular embodiments, propylene glycol, polyethylene glycol, ethoxy diglycol can be added to the composition in an amount of about 15% to about 30% by weight of the total composition.

In embodiments, product forms can be formulated to contain water in an amount of about 40% to about 99% by weight of the total composition. For example distilled water can be added to the composition in an amount of about 40% to about 99% by weight of the total composition. In particular embodiments, distilled water can be added to the composition in an amount of about 65% to about 80% by weight of the total composition.

In embodiments, organic peroxide compositions in accordance with the present disclosure are useful in the formation of oil-in-water emulsion product forms. Accordingly, the compositions may include an aqueous phase. Conventional emulsion formulation typically requires mixing the aqueous phase ingredients and the dispersant with heating until a uniform solution or dispersion is obtained (optionally in several stages), mixing the organic phase ingredients with heating until a uniform solution or dispersion is obtained (also optionally in several stages), then adding the aqueous phase to the organic phase with agitation (e.g. stirring or other shearing or heating technique) to form an oil-in-water emulsion of the two phases. However, heating steps are problematic in that heat decomposes organic peroxides such as benzoyl peroxide. The present compositions are capable of a low temperature blending and shearing techniques that do not require an intensive heating step. Accordingly, such blending can occur at room temperature.

In some emulsion embodiments, the aqueous phase constituting the dispersion medium may include any suitable surfactant, humectant, suspending agent, and/or buffer systems, and combinations thereof suitable for combining with organic peroxide compositions in accordance with the present disclosure.

Non-limiting examples of suitable surfactants include natural compounds, such as phospholipids and cholates, or nonnatural compounds such as: polysorbates, which are fatty acid esters of polyethoxylated sorbitol; polyethylene glycol esters of fatty acids from sources such as castor oil; polyethoxylated fatty acid, e.g. stearic acid; octylphenolpoly(ethyleneglycolether); polyethoxylated isooctylphenol/formaldehyde polymer; poloxamers, e.g., poly(oxyethylene)poly(oxypropylene) block copolymers; polyoxyethylene fatty alcohol ethers; polyoxyethylene nonylphenyl ethers; polyoxyethylene isooctylphenyl ethers; SDS, and combinations thereof.

In embodiments, non-limiting examples of suitable mixtures of surfactant molecules, including mixtures of surfactants of different chemical types, are acceptable. Surfactants should be suitable for cosmetic or pharmaceutical administration and compatible with the benzoyl peroxide to be delivered. Non-limiting examples of surfactants include phospholipids such as phosphatidylcholines (lecithins), including soy or egg lecithin. Other suitable phospholipids include phosphatidylglycerol, phosphatidylinositol, phosphatidylserine, phosphatidic acid, cardiolipin, and phosphatidylethanolamine. The phospholipids may be isolated from natural sources or prepared by synthesis.

Non-limiting examples of suitable suspending agents include the following constituents: polyacrylamide, C13-14 isoparafin & laureth 7; C13-14 isoparaffin, mineral oil, polyacrylate, polyacrylamide and ethoxylated sorbitan ester; acrylamide/sodium acryloyldimethyl taurate copolymer, isohexadecane and ethoxylated sorbitan ester; and combinations thereof. However any cosmetically or pharmaceutically acceptable suspending agent suitable for combining with benzoyl peroxide may be used.

Non-limiting examples of suitable humectants include glycerin, however any material capable of obtaining moisture may be added provided it is stable with organic peroxide.

The products formulated with the present solutions can be packaged in any type of container within the purview of those skilled in the art, including, but not limited to bottles, tubes, pump type, roll-ons, daubers, wipes, and the like.

The organic peroxide compositions in accordance with the present disclosure can be topically applied to skin in need of improvement in order to reduce or eliminate undesirable skin conditions. As used herein the word "treat," "treating" or "treatment" refers to using the compositions of the present disclosure prophylactically to prevent outbreaks of undesirable skin condition such as Acne Vulgaris, or therapeutically to ameliorate an existing undesirable skin condition. A number of different treatments are now possible, which reduce and/or eliminate skin conditions such as Acne Vulgaris.

As used herein "skin condition" refers to any detectable skin manifestations caused by one or more pathogens or microbes. Such manifestations can be compounded due to a number of factors such as, for example, chronological aging, environmental damage, and/or other diseased or dysfunctional state. Non-limiting examples of such manifestations include the development of skin lines, crevices, bumps, comedones, craters, scaliness, flakiness and/or other forms of skin unevenness, roughness, or mottled appearance. It is understood, that the listed skin conditions are non-limiting and that only a portion of the skin conditions suitable for treatment in accordance with the present disclosure are listed herein.

In embodiments, compositions for use in accordance with the present disclosure contain organic peroxide in an effective amount to improve undesirable skin conditions. As used herein "effective amount" refers to an amount of a compound or composition having organic peroxide constituents in accordance with the present disclosure that is sufficient to induce a particular positive benefit to skin having a skin condition. The positive benefit can be health-related, or it may be more cosmetic in nature, or it may be a combination of the two. In embodiments, the positive benefit is achieved by contacting skin with a combination of solvated organic peroxide, and/or one or more antibiotic constituents, to improve a skin condition such as Acne Vulgaris.

The particular organic peroxide concentration in the compositions generally depends on the purpose for which the composition is to be applied. For example, the dosage and frequency of application can vary depending upon the type and severity of the skin condition.

Treatments in accordance with the present disclosure contact skin with organic peroxide in an effective amount to improve acne related skin conditions. In embodiments, patients are treated by topically applying to skin suffering from an acne related condition, one or more organic peroxide compositions. The active ingredient is applied until the treatment goals are obtained. However, the duration of the treatment can vary depending on the severity of the condition. For example, treatments can last several weeks to months depending on whether the goal of treatment is to reduce or eliminate an acne related skin condition.

As used herein the term "stable" or "stability" refers to the ability of a material or composition to remain unchanged in the presence of heat, moisture or air. With respect to shelf life the terms further can refer to compositions that when in a closed container, remain within the tolerances and limits set forth in US Pharmacopoeia and/or the US FDA guidelines or monographs for compositions containing organic peroxides. The entire US Pharmacopoeia and collection of US FDA guidelines or monographs for compositions containing any particular organic peroxide or combination of active ingredients including at least one organic peroxide are too voluminous to present in their entirety herein and thus are instead incorporated in their entirety by this reference. With respect to topical compositions, the tolerances and limits are frequently presented relative to the labeled amount. With respect to benzoyl peroxide cream, for example, the acceptable tolerance is not less than 90.0 percent and not more than 125.0 percent of the labeled amount of $C_{14}H_{10}O_4$. Those skilled in the art will readily be able to identify the tolerances and limits for other compositions containing organic peroxides.

Treatments in accordance with the present disclosure contact skin with a stable mixture of organic peroxide and antioxidant in an effective amount to improve acne related skin conditions. In embodiments, patients are treated by topically applying to skin suffering from an acne related condition, one or more stable mixtures of organic peroxide and antioxidant.

In embodiments, the stable organic peroxides/antioxidant mixtures are applied for cosmetic purposes only.

In some embodiments, use of an antioxidant may be included in the manufacture of organic peroxide medicament such as benzoyl peroxide medicament for treatment of a skin condition. In some embodiments, antioxidants include any antioxidant described in the present disclosure. The organic peroxides include any organic peroxides described in the present disclosure. In some embodiments, the medicament include one or more stable mixtures of organic peroxides and antioxidants in accordance with the present disclosure. The medicament may include weight ratios of antioxidants to organic peroxide as described in the present disclosure.

The following non-limiting examples further illustrate compositions, methods, and treatments in accordance with the present disclosure. It should be noted that the disclosure is not limited to the specific details embodied in the examples.

EXAMPLE 1

A solution of benzoyl peroxide ("BPO") was formulated in the following manner to deliver 8% benzoyl peroxide in the finished product.

| Ingredient | Amount |
|---|---|
| Benzoyl Peroxide 75% wet with water | 10.67 to carry in 8 parts dry BPO |
| Benzoyl benzoate | 40.00% |

Benzoyl peroxide was dissolved into the benzyl benzoate. The resulting solution/dispersion was then added to the following materials.

| Ingredient | Amount |
|---|---|
| Ethoxydiglycol | 10.00 parts |
| Dimethyl Isosorbide | 41.1 parts |
| Butylated Hydroxytoluene (BHT) (antioxidant) | 0.40 parts |
| Vitamin E Acetate (antioxidant) | 0.50 parts |

The above formulation results in a clear solution that has pharmaceutical properties.

The thermal decomposition of benzoyl peroxide results in the generation of carbon dioxide gas as well as free radicals. The amount of carbon dioxide gas given off can be used as a relative measurement of the stability of any two compositions in relationship to each other.

The formula of Example 1 was placed on stability at elevated temperatures of 40° C. and 30° C. versus the same formula without the two antioxidants. The samples were placed in glass bottles with eye droppers. When samples are first made the dropper is completely empty of liquid, due to the seal of the bulb onto the bottle. Carbon dioxide gas, if any, generated by the benzoyl peroxide decomposition raises pressure in the bottle. As the pressure raises the glass dropper will fill with liquid, eventually filling the dropper and finally forcing the liquid into the dropper bulb. In extreme cases, the bulb will expand and then finally rupture if great pressures are present. Lack of liquid being forced into the dropper is considered an indication of very low levels of decomposition.

During the test period of a month at 40° C., the samples with the antioxidants had significantly less gas generated than the control sample, in which the liquid had pushed up into the bulb and eventually destroyed it. The test product dropper had only just filled and remained at bottle liquid height.

Many experiments were performed utilizing this procedure of comparing the formulas with and without individual as well as combinations of antioxidants. This test was sensitive enough to be able to pick up differences in solvent systems stability, the level of benzoyl peroxide, type antioxidant versus efficacy, temperature of storage, and levels of antioxidant in the samples. Conventional analytical testing confirmed the actual concentration of the remaining benzoyl peroxide.

EXAMPLE 2

A toner composition shown below was tested using the procedure described in Example 1.

| Ingredient | Amount |
| --- | --- |
| Benzoyl Peroxide 75% wet with water | 3.33% to carry in 2.5% BPO dry |
| Ethoxydiglycol | 25.00% |
| Benzyl benzoate | 42.47% |
| Dimethyl isosorbide | 21.6% |
| Benzoic acid | 5.00% |
| Salicylic acid | 2.00% |
| Vitamin E Acetate | 0.2% |
| Butylated hydroxyl toluene | 0.4% |

The test formula above was placed on stability at elevated temperatures of 40° C. and 30° C. versus a control formulation (the same formula above without the two antioxidants). The samples were placed in glass bottles with eye droppers and checked for the amount of gas that was generated. After a month at 40° C. the control samples (the same formula above without the two antioxidants) had filled up into the rubber bulb and pressure was evident via bulb expansion. In the case of the test formula, the droppers were empty and liquid had not moved into bulb. For the 30° C. samples the control had completely filled the dropper and was present in the bulb. The dropper of the above test formula was completely empty of fluid at 30° C. The results of Example 2 where less dramatic than Example 1 (where the bulb was destroyed) because Example 2 had lower levels of benzyl peroxide in the toner formula.

EXAMPLE 3

Another formulation in accordance with the present disclosure is as follows:

| Ingredient | Amount |
| --- | --- |
| Benzoyl Peroxide | 6.25% |
| Benzoyl benzoate | 42.45% |
| Dimethyl isosorbide | 40.00% |
| Vitamin E Acetate | 0.5% |
| BHT | 0.8% |
| Ethoxy diglycol | 10.0% |
| fumed silica | 0-10% |

EXAMPLE 4

An emulsion formulation in accordance with the present disclosure is prepared by combining the following two phases A and B:

| Phase A Ingredients | Amount |
| --- | --- |
| Benzoyl Peroxide 75% wet with water | 8.68% |
| Benzyl Benzoate | 10.00% |
| BHT | 0.4% |
| Vitamin E Acetate | 0.5% |
| Dimethyl Isosorbide | 3.00% |

Phase A is made by adding benzoyl peroxide to container with the Benzyl Benzoate, BHT and Vitamin E Acetate and mixing for 30 minutes. The dimethyl isosorbide is then added with mixing for an additional ten minutes.

| Phase B Ingredients | Amount |
| --- | --- |
| DI Water | 74.22% |
| Phenoxyethanol | 0.1% |
| EDTA disodium salt | 0.1% |
| Simulgel NS* | 3.0% |

*(Hydroxyethyl acrylate/sodium acryloyidimethyl taurate copolymer, squalane and polysorbate 60.)

The phase B ingredients are added together and mixed. Phase A is added to Phase B under high shear mixing until uniform emulsion (oil-in-water) is formed. Other materials with desired properties may be added, provided they are stabile with organic peroxide.

It will be understood that various modifications may be made to the embodiments disclosed herein. Therefore, the above description should not be construed as limiting, but merely as exemplifications of embodiments. Those skilled in art will envision other modifications within the scope and spirit of the claims appended hereto.

What is claimed is:

1. An emulsion composition comprising:
   an aqueous phase; and
   an organic phase comprising benzoyl peroxide, an antioxidant and an aryl benzoate ester,
   each of the aqueous phase and organic phase being suitable for topical application to the skin of a user.

2. An emulsion composition as in claim 1 wherein the organic phase is a solution.

3. An emulsion composition as in claim 1 wherein the organic phase is a dispersion.

4. An emulsion as in claim 1 wherein the antioxidant is selected from butylated hydroxyl toluene (BHT), butylated hydroxyanisole (BHA), vitamin E acetate, ascorbyl palmitate, tetrahydrocurcuminoids, t-butyl hydroquinone, meta and para cresols, phenolics, and combinations thereof.

5. An emulsion according to claim 1 wherein the aqueous phase comprises at least one component selected from the group consisting of surfactant, humectant, suspending agent, buffer system, and combinations thereof.

6. An emulsion as in claim 1 wherein the organic phase comprises less than 2% antioxidant by weight of the composition, and no more than about 10% benzoyl peroxide by weight of the composition.

7. An emulsion as in claim 1 wherein the organic phase about 5% antioxidant by weight of the composition, and no more than about 20% benzoyl peroxide by weight of the composition.

8. An emulsion as in claim 1 wherein the amount of benzoyl peroxide present exceeds the solubility limit of benzoyl peroxide in the aryl benzoate ester.

9. An emulsion comprising:
   an aqueous phase; and
   an organic phase comprising a dispersion comprising benzoyl peroxide, an antioxidant and benzyl benzoate in an amount insufficient to completely solubilize the benzoyl peroxide,
   each of the aqueous phase and organic phase being suitable for topical application to the skin of a user.

10. A method comprising:
    combining benzoyl peroxide, an antioxidant and benzyl benzoate in an amount insufficient to completely solubilize the benzoyl peroxide at room temperature to provide an organic phase;

mixing the dispersion with an aqueous phase to form an emulsion.

11. The method of claim 10 wherein the aqueous phase comprises at least one component selected from the group consisting of surfactant, humectant, suspending agent, buffer system, and combinations thereof.

12. The method of claim 10 wherein the aqueous phase contains glycerin.

13. A method of treating acne comprising applying an emulsion in accordance with claim 9 to the skin of a subject afflicted with acne.

* * * * *